US007632944B2

(12) United States Patent
Harms

(10) Patent No.: US 7,632,944 B2
(45) Date of Patent: *Dec. 15, 2009

(54) QUINOLONE CARBOXYLIC ACIDS, DERIVATIVES THEREOF, AND METHODS OF MAKING AND USING SAME

(75) Inventor: Arthur E. Harms, Fairport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 15 days.

This patent is subject to a terminal disclaimer.

(21) Appl. No.: 11/626,397

(22) Filed: Jan. 24, 2007

(65) Prior Publication Data

US 2008/0176834 A1 Jul. 24, 2008

(51) Int. Cl.
*C07D 223/00* (2006.01)
(52) U.S. Cl. .................................................. 540/484
(58) Field of Classification Search ................ None
See application file for complete search history.

(56) References Cited

U.S. PATENT DOCUMENTS

| 5,385,900 | A | 1/1995 | Konno et al. |
| 5,447,926 | A | 9/1995 | Konno et al. |
| 6,685,958 | B2 | 2/2004 | Roy et al. |
| 6,699,492 | B2 | 3/2004 | Roy et al. |

FOREIGN PATENT DOCUMENTS

| EP | 0230946 A2 | 8/1987 |
| EP | 0493608 A1 | 7/1992 |
| EP | 0601197 A1 | 6/1994 |
| FR | 2706459 A1 | 12/1994 |
| JP | 63132885 A | 6/1988 |
| JP | 63196579 A | 8/1988 |
| JP | 63196580 A | 8/1988 |
| WO | WO 94/15933 A1 | 7/1994 |

OTHER PUBLICATIONS

Araki et al., "Quinolone antimicrobial agents substituted with morpholines at the 7-position. Syntheses and structure—activity relationships," J Med Chem, 1993, (vol. 36), (p. 1356-1363).

Takei et al., "Target Preference of 15 Quinolones Against *Staphylococcus aureus*, Based on Antibacterial Activities and Target Inhibition," Antimicrobial Agents and Chemotherapy, Dec. 2001, vol. 45 ( No. 12), p. 3544-3547.

Oizumi et al., "Relationship Between Mutations in the DNA Gyrase and Topoisomerase IV Genes and Nadifloxacin Resistance in Clinically Isolated Quinolone-Resistant *Staphylococcus aureus*," J. Infect. Chemother., 2001, p. 191-194.

Adamson, "The Anhydrides of Basic Amino-acids," Dyson Perrins Laboratory, Oxford University, p. 39-40, (Nov. 17, 1942).

Pellegata et al., "An Improved Synthesis of y-,o-, and e-Lactams," Communications, 1978, Georg Thieme Publishers, p. 614-616.

Saburi et al., "Stereochemical Properties of Copper (II) Complexes of (X)-3-Aminohexahydroazepine, Crystal and Molecular Structure of Bromobis[(S)-3-aminohexahydroazepine]copper(II) Perchlorate [CuBr(S-ahaz)2]C1O4," Bull. Chem. Soc. of Japan, Jan. 1987, p. 141-148.

Chong et al., "Stereoselective and Regioselective Synthesis of Azepane and Azepine Derivatives via Piperidine Ring Expansion," J. Chem. Soc., Perkin Trans., 2002, p. 2080-2086.

Barluenga, "Fischer Carbene Complexes. A New Tool for Heterocyclic Synthesis," Pure Appl. Chem., 2002, vol. 74 ( No. 8), p. 1317-1325.

Naito et al., "A Novel and Chiral Synthesis of Both Enantiomers of Trans-3-Amino-4-Hydroxyhexahydroazepine, a Key Intermediate fo the Synthesis of Balanol," Kobe Pharm. University, www.ch.ic.ac. uk/ectoc/echet96/papers/054/index.htm, 2006.

*Primary Examiner*—James O Wilson
*Assistant Examiner*—Noble Jarrell
(74) *Attorney, Agent, or Firm*—Toan P. Vo

(57) ABSTRACT

A process of preparing a quinolone carboxylic acid or its derivatives having Formula I, Ia, or IV, as shown herein, comprises using a starting quinolone that already has one or more desired substituents at one or more particular positions on the quinolone ring and preserving the orientation of such substituents throughout the synthesis. The present process comprises fewer steps than prior-art processes. The present process also can include a simple separation of a desired enantiomer of the quinolone carboxylic acid or its derivatives from the enantiomeric mixture. Pharmaceutical compositions comprising fluoroquinolones prepared by the present process can be used effectively against a variety of microbial pathogens.

9 Claims, No Drawings

QUINOLONE CARBOXYLIC ACIDS, DERIVATIVES THEREOF, AND METHODS OF MAKING AND USING SAME

BACKGROUND OF THE INVENTION

The present invention relates to quinolone carboxylic acids, derivatives thereof, and methods of making and using the same. In particular, the present invention relates to fluoroquinolone carboxylic acids, derivatives thereof, methods of making and using the same.

Bacterial pathogens continue to pose a serious threat to public health as indicated by a worldwide resurgence of bacterial diseases. One aspect of this resurgence appears to be the result of prior widespread, and largely effective, therapeutic and prophylactic use of antibiotics, which, unfortunately, over time has also selected for resistant strains of various bacterial pathogens. Of particular concern to the public health has been the emergence and proliferation of bacterial strains that are resistant to multiple antibiotics in the current arsenal of antimicrobial agents. Such multiantibiotic-resistant ("MAR") bacterial strains include species of Gram-positive bacteria, such as, antibiotic-resistant strains of *Staphylococcus aureus, Enterococcus fecalis,* and *Enterococcus fectum,* which, along with antibiotic-resistant Gram-negative strains of *Escherichia coil,* constitute the most frequent etiological agents of nosocomial (hospital-acquired) diseases, such as septicemia, endocarditis, and infections of wounds and the urinary tract. *S. aureus* is currently the most frequent cause of nosocomial bacteremia and skin or wound infection. *Streptococcus pneumoniae* causes several serious and life-threatening diseases, including a contagious meningitis, bacteremia, and otitis media. Annual mortality from *S. pneumoniae* infection alone is estimated at between 3-5 million persons globally. More recently, clinical accounts of highly aggressive skin and tissue infections by "flesh-eating" strains of Group-A *streptococcus* bacteria, such as *Streptococcus pyogenes,* has heightened the concern and need for new or improved antibacterial agents.

Quinolones constitute a group of antibiotics that have been available since the early 1960s and have proved to be valuable antibacterial agents. Quinolone carboxylic acid derivatives having various chemical structures have been synthesized, developed, and marketed. Nalidixic acid (1,4-dihydro-1-ethyl-7-methyl-1,8-naphthyridin-4-one-3-carboxylic acid), the progenitor of the series, was used primarily as a urinary-tract antiseptic. Later development provided agents with broader activity, increased potency against selected pathogens and improved pharmacokinetic and pharmacodynamic properties.

From a medical utility viewpoint, the quinolones are classified as first-, second-, and third-generation compounds. First-generation compounds like piromidic acid (8-ethyl-5,8-dihydro-5-oxo-2-(1-pyrrolidinyl)pyrido(2,3-d)pyrimidine-6-carboxylic acid) and pipemidic acid (8-ethyl-5,8-dihydro-5-oxo-2-(1-piperazinyl)pyrido(2,3-d)pyrimidine-6-carboxylic acid) provided coverage for Gram-negative *Enterobacteriaceae.* The second-generation compounds are divided into those with enhanced but predominant Gram-negative activity, against pathogens like *Escherichia coli* and *Pseudomonas aeruginosa,* and those with balanced broad-spectrum activity (norfloxacin, pefloxacin, enoxacin, fleroxacin, lomefloxacin, ciprofloxacin, ofloxacin, rufloxacin, nadifloxacin). Norfloxacin, ofloxacin, and ciprofloxacin have, therefore, been used mainly for treatment of diseases including urinary tract infections, gastrointestinal infections, sexually transmitted diseases and the like. Third-generation antibiotics (levofloxacin, pazufloxacin, sparfloxacin, clinafloxacin, sitafloxacin, trovafloxacin, tosufloxacin, temafloxacin, grepafloxacin, balofloxacin, moxifloxacin, gatifloxacin) are those with enhanced activity against Gram-positive cocci (notably clinafloxacin, sitafloxacin, trovafloxacin for *Streptococcus pneumoniae*) and, for essentially all the third-generation quinolones, activity also against Gram-negative *Haemophilus influenzae* and *Legionella pneumophila,* and against anaerobes and atypical pathogens. Levofloxacin, moxifloxacin, and gatifloxacin have, therefore, found use for community-acquired infections such as those of the upper and lower respirator) tract infections ("RTI") like pneumonia, sinusitis and pharyngitis, and for skin and soft tissue infections ("SSI") caused by Gram-positive strains of *staphylococci, pneumococci, streptococci,* and *enterococci.*

The improvements seen in most of the third-generation antibiotics in current use are generally attributed to their uniqueness in inhibiting DNA gyrase and topoisomerase IV of the bacterial targets. Three categories of quinolone inhibition have been suggested. Type I quinolones (norfloxacin, enoxacin, fleroxacin, ciprofloxacin, lomefloxacin, trovafloxacin, grepafloxacin, ofloxacin and levofloxacin) indicate a preference for topoisomerase IV inhibition. Type II quinolones (nadifloxacin and sparfloxacin) indicate a preference for DNA gyrase inhibition. Type III quinolones to which some of the third-generation quinolones belong (e.g., gatifloxacin, pazufloxacin, moxifloxacin and clinafloxacin) display, however, a dual-targeting property, and equally influence DNA gyrase inhibition and topoisomerase IV inhibition. (M. Takei, et al. *Antimicrobial Agents and Chemotherapy,* Vol. 45, 3544-49 (2000)). DNA gyrase is the primary target in bacteria, and thus is explained the weaker activity in Gram-positive bacteria of the topoisomerase IV-targeting second-generation quinolones like norfloxacin, ciprofloxacin, ofloxacin, and levofloxacin. The unusual activity of nadifloxacin described in the literature, especially against Gram-positive *S. aureus,* now can be explained by its ability to target DNA gyrase (N. Oizumi, et al., *J. Infect. Chemother.,* Vol. 7, 191-194 (2001)). That some third-generation quinolones are primarily capable of targeting topoisomerase IV in Gram-positive *staphylococci,* and DNA gyrase in Gram-positive *S. pneumoniae,* explains the advantages provided by the dual-targeting third-generation quinolones like moxifloxacin and gatifloxacin. However, because of continuing threat of new strains of antibiotic-resistant bacteria that may surface in the future, continued effort has been devoted to develop new broad-spectrum antibiotics.

A family of fluoroquinolones was recently developed, and some compounds of this family show good antimicrobial activity against a wide range of Gram-positive and Gram-negative bacteria. See U.S. Pat. Nos. 5,385,900; 5,447,926; 6,685,958; and 6,699,492; all of which are incorporated herein by reference in their entirety. Because of the promise of their therapeutic value, it is very desirable, in one aspect to develop improved processes for preparing this family of fluoroquinolones in order to allow for a more widespread availability of these compounds.

SUMMARY OF THE INVENTION

In general, the present invention provides an improved process for preparing fluoroquinolones that have Formula I or salts thereof.

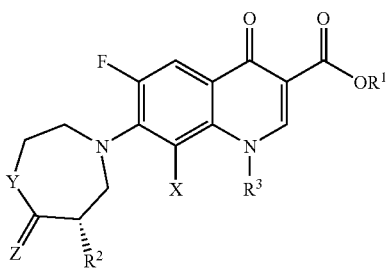

wherein R¹ is selected from the group consisting of hydrogen, unsubstituted lower alkyl groups, substituted, lower alkyl groups, cycloalkyl groups, unsubstituted $C_5$-$C_{24}$ aryl groups, substituted $C_5$-$C_{21}$ aryl groups, unsubstituted $C_5$-$C_{24}$ heteroaryl groups, substituted $C_5$-$C_{24}$ heteroaryl groups, and groups that can be hydrolyzed in living bodies; R² is selected from the group consisting of hydrogen, unsubstituted amino group, and amino groups substituted with one or two lower alkyl groups; R³ is selected from the group consisting of hydrogen, unsubstituted lower alkyl groups, substituted lower alkyl groups, cycloalkyl groups, unsubstituted lower alkoxy groups, substituted lower alkoxy groups, unsubstituted $C_5$-$C_{24}$ aryl groups, substituted $C_5$-$C_{24}$ and groups, unsubstituted $C_5$-$C_{24}$ heteroaryl groups, substituted $C_5$-$C_{24}$ heteroaryl groups, unsubstituted $C_5$-$C_{24}$ aryloxy groups, substituted $C_5$-$C_{24}$ aryloxy groups, unsubstituted $C_3$-$C_{24}$ heteroaryloxy groups, substituted $C_5$-$C_{24}$ heteroaryloxy groups, and groups that can be hydrolyzed in living bodies; X is selected from the group consisting of halogen atoms; Y is selected from the group consisting of $CH_2$, O, S, SO, $SO_2$, and NR⁴, wherein R⁴ is selected from the group consisting of hydrogen, unsubstituted lower alkyl groups, substituted lower alkyl groups, and cycloalkyl groups; and Z is selected from the group consisting of oxygen and two hydrogen atoms.

In one aspect, a process of preparing fluoroquinolones having Formula I comprises contacting a first compound having Formula II with a second compound having Formula III to produce a fluoroquinolone having Formula I, wherein the first compound and the second compound are represented by

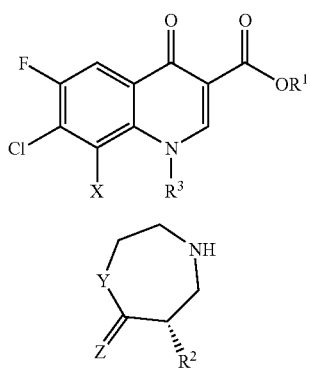

wherein R¹, R², R³, X, Y, and Z have the meanings as disclosed above.

In another aspect, a process of preparing fluoroquinolones having Formula IV comprises: (a) contacting a first compound having Formula II with a third compound having Formula V to produce a fourth compound having Formula VI, wherein the fluoroquinolones having Formula IV, the first compound, the third compound, and the fourth compound are represented by

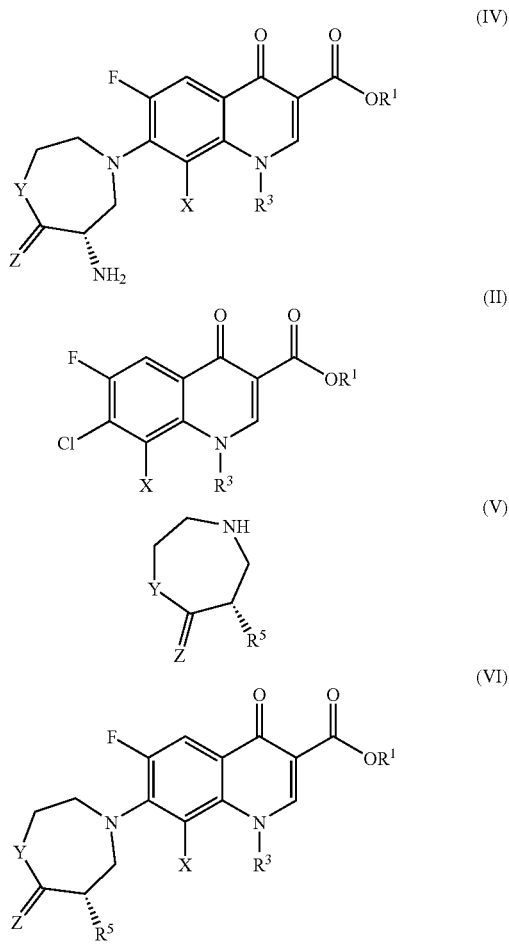

wherein R¹, R³, X, Y, and Z have the meanings as disclosed above and R⁵ comprises a protected amino group having a formula of —NR⁶, wherein R⁶ comprises a protecting group that is capable of leaving the protected amino group —NR⁶, and (b) contacting the fourth compound with a catalyst to effect a cleavage of the protecting group from the —NR⁶ group, to produce a fluoroquinolone having Formula IV.

In a further aspect, the present invention provides a process for preparing fluoroquinolones having Formula I. The process comprises: (a) contacting a compound having Formula XIII with a compound having Formula III to produce a compound having Formula XIV; and (b) halogenating the compound having Formula XIV with a halogenating agent to produce the fluoroquinolones having Formula I; wherein R¹ is selected from the group consisting of hydrogen, unsubstituted lower alkyl groups, substituted lower alkyl groups, cycloalkyl groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, and groups that can be hydrolyzed in living bodies; R² is selected from the group consisting of hydrogen, unsubstituted amino group, and amino groups substituted with one or two lower alkyl groups; R³ is selected from the group consisting of hydrogen, unsubstituted lower alkyl groups, substituted lower alkyl groups, cycloalkyl groups, unsubstituted lower alkoxy groups, substituted lower alkoxy groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, unsubstituted $C_5$-$C_{24}$ aryloxy groups, substituted $C_5$-$C_{24}$ aryloxy groups, unsubstituted $C_5$-$C_{24}$ heteroaryloxy groups, substituted $C_5$-$C_{24}$ heteroaryloxy groups, and groups that can be hydrolyzed in living bodies; X is selected from the group consisting of halogen atoms; Y is selected from the group consisting of $CH_2$, O, S, SO, $SO_2$, and $NR^4$, wherein $R^4$ is selected from the group consisting of hydrogen, unsubstituted lower alkyl groups, substituted lower alkyl groups, and cycloalkyl groups; and Z is selected from the group consisting of oxygen and two hydrogen atoms. The compounds having Formulae XIII, III, and XIV are shown below.

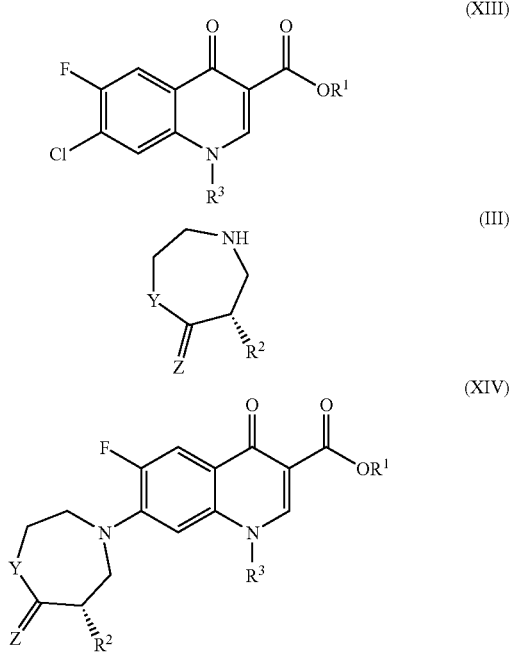

In a further aspect, the present invention provides quinolone carboxylic acids prepared by any process disclosed herein and their derivatives (such as their salts or esters), and methods of using such quinolone carboxylic acids and derivatives.

Other features and advantages of the present invention will become apparent from the following detailed description and claims.

DETAILED DESCRIPTION

As used herein, the term "lower alkyl" or "lower alkyl group" means a $C_1$-$C_{15}$ linear- or branched-chain saturated aliphatic hydrocarbon monovalent group, which may be unsubstituted or substituted. The group may be partially or completely substituted with halogen atoms (F, Cl, Br, or I). Non-limiting examples of lower alkyl groups include methyl, ethyl, n-propyl, 1-methylethyl(isopropyl), n-butyl, n-pentyl, 1,1-dimethylethyl(t-butyl), and the like. It may be abbreviated as "Alk".

As used herein, the term "lower alkoxy" or "lower alkoxy group" means a $C_1$-$C_{15}$ linear- or branched-chain saturated aliphatic alkoxy monovalent group, which may be unsubstituted or substituted. The group may be partially or completely substituted with halogen atoms (F, Cl, Br, or I). Non-limiting examples of lower alkoxy groups include methoxy, ethoxy, n-propoxy, 1-methylethoxy(isopropoxy), n-butoxy, n-pentoxy, t-butoxy, and the like.

The term "cycloalkyl" or "cycloalkyl group" means a stable aliphatic saturated 3- to 15-membered monocyclic or polycyclic monovalent radical consisting solely of carbon and hydrogen atoms which may comprise one or more fused or bridged ring(s), preferably a 3- to 7-membered monocyclic rings. Other exemplary embodiments of cycloalkyl groups include 7- to 10-membered bicyclic rings. Unless otherwise specified, the cycloalkyl ring may be attached at any carbon atom which results in a stable structure and, if substituted, may be substituted at any suitable carbon atom which results in a stable structure. Exemplary cycloalkyl groups include cyclopropyl, cyclobutyl, cyclopentyl, cyclohexyl, cycloheptyl, cyclooctyl, cyclononyl, cyclodecyl, norbornyl, adamantyl, tetrahydronaphthyl(tetralin), 1-decalinyl, bicyclo[2.2.2]octanyl, 1-methylcyclopropyl, 2-methylcyclopentyl, 2-methylcyclooctyl, and the like.

As used herein, the term "aryl" or "aryl group" means an aromatic carbocyclic monovalent or divalent radical. In some embodiments, the aryl group has a number of carbon atoms from 5 to 24 and has a single ring (e.g., phenyl or phenylene), multiple condensed rings (e.g., naphthyl or anthranyl), or multiple bridged rings (e.g., biphenyl). Unless otherwise specified, the aryl ring may be attached at any suitable carbon atom which results in a stable structure and, if substituted, may be substituted at any suitable carbon atom which results in a stable structure. Non-limiting examples of aryl groups include phenyl, naphthyl, anthryl, phenanthryl, indanyl, indenyl, biphenyl, and the like. It may be abbreviated as "Ar".

The term "heteroaryl" or "heteroaryl group" means a stable aromatic monocyclic or polycyclic monovalent or divalent radical, which may comprise one or more fused or bridged ring(s). In some embodiments, the heteroaryl group has 5-24 members, preferably a 5- to 7-membered monocyclic or 7- to 10-membered bicyclic radical. The heteroaryl group can have from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Non-limiting examples of heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl, diazaindolyl, dihydroindolyl, dihydroazaindoyl, isoindolyl, azaisoindolyl, benzofuranyl, furanopyridinyl, furanopyrimidinyl, furanopyrazinyl, furanopyridazinyl, dihydrobenzofuranyl, dihydrofuranopyridinyl, dihydrofuranopyrimidinyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, benzoxazinyl, benzoxazinonyl, oxazolopyridinyl, oxazolopyrimidinyl, benzisoxazolyl, purinyl chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like.

In general, the present invention provides an improved process for preparing fluoroquinolones that have Formula I or salts thereof.

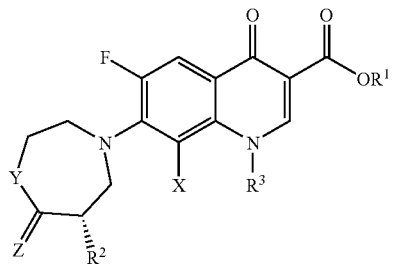

(I)

wherein $R^1$ is selected from the group consisting of hydrogen, unsubstituted lower alkyl groups, substituted, lower alkyl groups, cycloalkyl groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, and groups that can be hydrolyzed in living bodies; $R^2$ is selected from the group consisting of hydrogen, unsubstituted amino group, and amino groups substituted with one or two lower alkyl groups; $R^3$ is selected from the group consisting of hydrogen, unsubstituted lower alkyl groups, substituted lower alkyl groups, cycloalkyl groups, unsubstituted lower alkoxy groups, substituted lower alkoxy groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, unsubstituted $C_5$-$C_{24}$ aryloxy groups, substituted $C_5$-$C_{24}$ aryloxy groups, unsubstituted $C_5$-$C_{24}$ heteroaryloxy groups, substituted $C_5$-$C_{24}$ heteroaryloxy groups, and groups that can be hydrolyzed in living bodies; X is selected from the group consisting of halogen atoms; Y is selected from the group consisting of $CH_2$, O, S, SO, $SO_2$, and $NR^4$, wherein $R^4$ is selected from the group consisting of hydrogen, unsubstituted lower alkyl groups, substituted lower alkyl groups, and cycloalkyl groups; and Z is selected from the group consisting of oxygen and two hydrogen atoms.

In one aspect, $R^1$ is selected from the group consisting of hydrogen, $C_1$-$C_5$ (or alternatively, $C_1$-$C_3$) substituted and unsubstituted alkyl groups, $C_3$-$C_{10}$ (or alternatively, $C_3$-$C_5$) cycloalkyl groups, $C_5$-$C_{14}$ (or alternatively, $C_6$-$C_{14}$, or $C_5$-$C_{10}$, or $C_6$-$C_{10}$) substituted and unsubstituted aryl groups, $C_5$-$C_{14}$ (or alternatively, $C_6$-$C_{14}$, or $C_5$-$C_{10}$, or $C_6$-$C_{10}$) substituted and unsubstituted heteroaryl groups, and groups that can be hydrolyzed in living bodies. In one embodiment, $R^1$ is selected from the group consisting of $C_1$-$C_5$ (or alternatively, $C_1$-$C_3$) substituted and unsubstituted alkyl groups.

In another aspect, $R^2$ is selected from the group consisting of unsubstituted amino group and amino groups substituted with one or two $C_1$-$C_5$ (or alternatively, $C_1$-$C_3$) alkyl groups.

In still another aspect, $R^3$ is selected from the group consisting of hydrogen, $C_1$-$C_5$ (or alternatively, $C_1$-$C_3$) substituted and unsubstituted alkyl groups, $C_3$-$C_{10}$ (or alternatively, $C_3$-$C_5$) cycloalkyl groups, $C_1$-$C_5$ (or alternatively, $C_1$-$C_3$) substituted and unsubstituted alkoxy groups, $C_5$-$C_{14}$ (or alternatively, $C_6$-$C_{14}$, or $C_5$-$C_{10}$, or $C_6$-$C_{10}$) substituted and unsubstituted aryl groups, $C_5$-$C_{14}$ (or alternatively, $C_6$-$C_{14}$, or $C_5$-$C_{10}$, or $C_6$-$C_{10}$) substituted and unsubstituted heteroaryl groups, and $C_5$-$C_{14}$ (or alternatively, $C_6$-$C_{14}$, or $C_5$-$C_{10}$, or $C_6$-$C_{10}$) substituted and unsubstituted aryloxy groups. In one embodiment, $R^3$ is selected from the group consisting of $C_3$-$C_{10}$ (or alternatively, $C_3$-$C_5$) cycloalkyl groups.

In yet another aspect, X is selected from the group consisting of Cl, F, and Br. In one embodiment, X is Cl. In another embodiment, X is F.

In a further aspect, Y is hydrogen. In still another aspect, Z comprises two hydrogen atoms.

In one embodiment, the fluoroquinolone carboxylic acid has a Formula Ia.

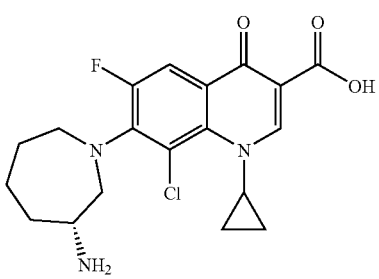

(Ia)

In one aspect, the present invention provides an improved process of preparing fluoroquinolones having Formula I. The process comprises contacting a first compound having Formula II with a second compound having Formula III to produce a fluoroquinolone having Formula I, wherein the first compound and the second compound are represented by

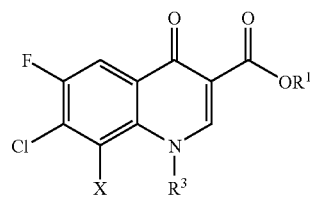

(II)

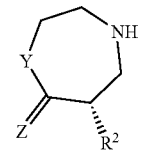

(III)

wherein $R^1$, $R^2$, $R^3$, X, Y, and Z have the meanings as disclosed above.

In another aspect, the first compound having Formula II, which is used in a process of the present invention as disclosed above, can be prepared according a procedure disclosed in published European Patent Application EP 0230946 A2, which is incorporated in its entirety by reference. For example, the first compound having Formula II is prepared by a process comprising: (a) reacting a compound having Formula X with an equimolar or excess amount of orthoformic acid ester in acetic anhydride (1 to 20-fold volume per total volume of the other reagents) at a temperature in the range from about room temperature to about 200° C. (preferably, from about 100° C. to about 150° C.) for a time from about 30 minutes to 24 hours to produce a compound having Formula XI; (b) treating the compound having Formula XI with an equimolar or excess amount of an amine having a formula of $NH_2R^3$ in a solvent comprising an alcohol (preferably, ethanol or propanol), to convert the compound having Formula XI to a compound having Formula XII; (c) treating the compound having Formula XII with a fluoride salt (such as one selected from the group consisting of sodium fluoride, potassium fluoride, and lithium fluoride) in a solvent selected from the group consisting of dioxane, dimethylformamide, dimethylsulfoxide, and sulfolane a temperature in the range from about 0° C. to about 200° C. (preferably, from about 50° C. to about 150° C.) for a time in the range from about 30 minutes to about 24 hours, to produce the compound having Formula II. The compounds having Formulae X, XI and XII are shown below.

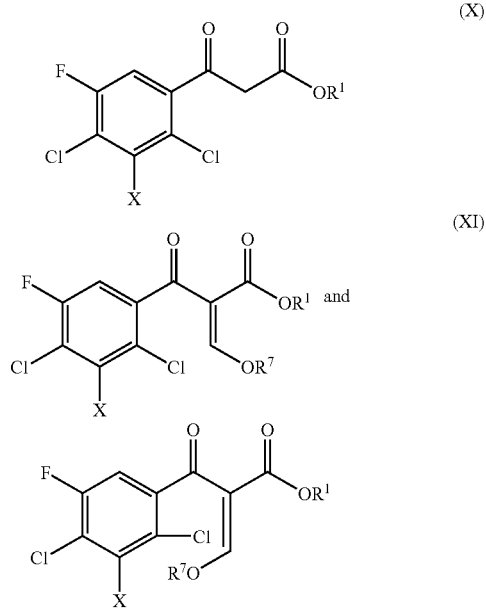

wherein $R^7$ is unsubstituted lower alkyl groups, substituted lower alkyl groups, unsubstituted $C_5$-$C_{24}$ aryl groups (or alternatively, $C_5$-$C_{14}$, or $C_5$-$C_{10}$, or $C_6$-$C_{10}$), cycloalkyl groups, substituted $C_5$-$C_{24}$ and groups (or alternatively, $C_5$-$C_{14}$, or $C_5$-$C_{10}$, or $C_6$-$C_{10}$), unsubstituted $C_5$-$C_{24}$ heteroaryl groups (or alternatively, $C_5$-$C_{14}$, or $C_5$-$C_{10}$, or $C_6$-$C_{10}$), and substituted $C_5$-$C_{24}$ heteroaryl groups (or alternatively, $C_5$-$C_{14}$, or $C_5$-$C_{10}$, or $C_6$-$C_{10}$); and

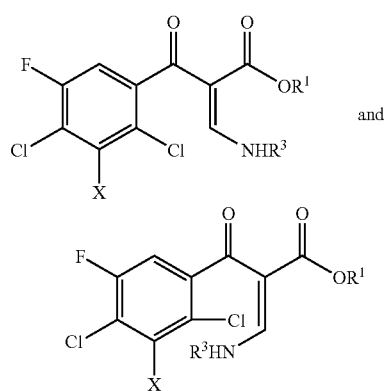

In another aspect, the second compound having Formula III can be prepared by cyclization of various amino acids. For examples, such compounds having Formula III can be prepared according to the methods disclosed in D. W. Adamson, *J. Chem. Soc.*, p. 39 (1943); R. Pellegata et al., *Synthesis*, p. 614 (1978); and M. Saburi et al., *Bull. Chem. Soc. Japan*, Vol. 60, pp 141-48 (1987). These references are incorporated herein by reference. Alternatively, various azepines having general Formula III can be prepared according to the methods disclosed in H. Chong et al., *J. Chem. Soc. Perkin Trans.*, Vol. 1, 2080-86 (2002); J. Barluenga, *Pure Appl. Chem.*, Vol. 74, No. 8, 1317-25 (2002); and T. Naito et al. (available at http://www.ch.ic.ac.uk/etoc/echet96/papers/054/index.htm. Electronic Conference on Heterocyclic Chemistry, Jun. 24 to Jul. 22, 1996, visited on Dec. 22, 2006), using appropriate starting materials. The references by H. Chong et al., and by J. Barluenga are incorporated herein by reference.

In one embodiment of the present invention, a fluoroquinolone having Formula I is prepared as follows. One mole of the compound having Formula II is reacted with about 1-5 moles of the compound having Formula III in a solvent such as acetonitrile, dimethylsulfoxide, or the like, at a temperature in the range from about room temperature to about 100° C. for a time in the range from about 10 minutes to about 7 days. After the reaction, the precipitate is collected by filtration and washed, for example at room temperature, with a sufficient quantity of a suitable solvent, such as methanol, chloroform, ether, or the like, to obtain a crude product. The crude product is purified, for example, by silica gel column chromatography or by recrystallization to obtain the fluoroquinolone having Formula I.

In another embodiment of the present invention, a fluoroquinolone having formula IV is prepared as follows. One mole of the compound having Formula II is reacted with about 1-5 moles of the compound having Formula V in a solvent such as acetonitrile, dimethylsulfoxide, or the like, at a temperature in the range from about room temperature to about 100° C. for a time in the range from about 10 minutes to about 7 days to produce a compound having Formula VI. An amount of an acid or base (depending on whether the cleavage of the protecting group is acid- or base-catalyzable), such as from about 0.1 to about 5 moles per mole of the compound having Formula V, is added to the reaction mixture to allow for the splitting of the protecting group $R^6$ from the protected amino —$NR^5$ group. In one embodiment, after this reaction, a base is added to the reaction mixture to convert free HF and HX acids to their salts (resulting pH is about 7), which are washed, for example at room temperature, from the mixture to produce a crude product. The crude product is purified, for example, by silica gel column chromatography or by recrystallization to obtain the fluoroquinolone having Formula IV.

In one embodiment, the compound having general Formula V has particular Formula VII.

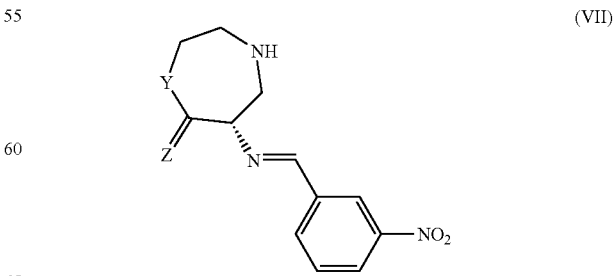

This compound can be prepared by the following reaction.

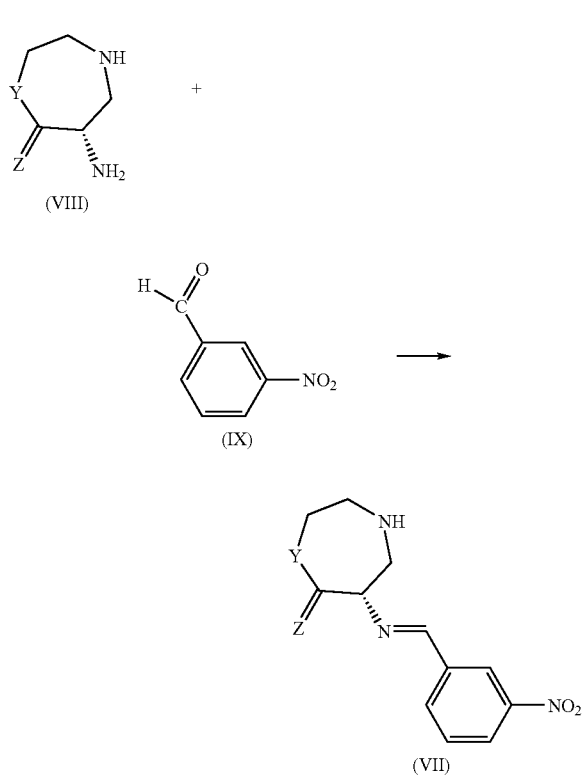

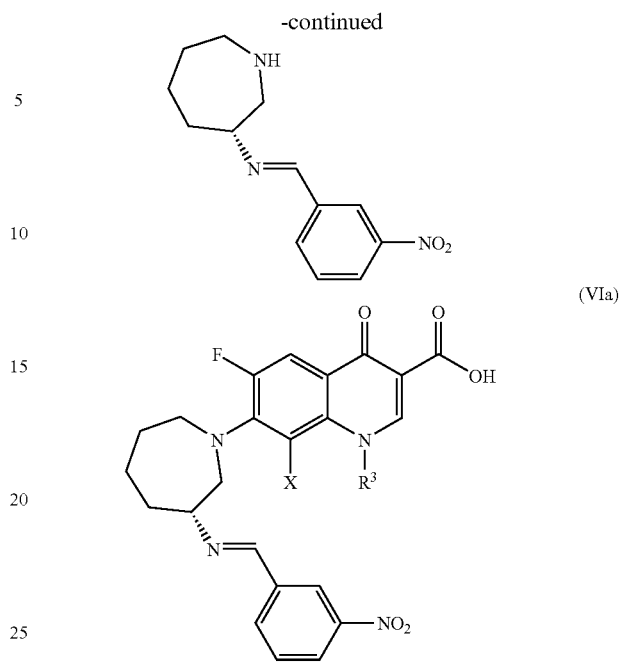

The nitrophenylalkylidene protecting group is disclosed in the above scheme only for illustrative purposes. Other protecting groups can be used in place of the nitrophenylalkylidene group, as can be recognized by people having skill in the art of organic synthesis. For example, another commonly used protecting group for the amine moiety is the t-butoxycarbonyl ("t-Boc"), which may be finally cleaved by an anhydrous acid catalyst, such as HCl to yield the amino group. Still another example of a protecting group for the amine moiety is the fluorenylmethoxycarbonyl ("Fmoc"), which can be cleaved by an anhydrous base catalyst, such as ammonia, piperidine, or morpholine.

In still another aspect, a process for preparing a fluoroquinolone carboxylic acid having Formula Ia comprises: (a) contacting a compound having Formula IIa with a compound having Formula VIIa at a temperature in the range from about room temperature to about 100° C. for a time from about 10 minutes to about 7 days, to produce a compound having Formula VIa

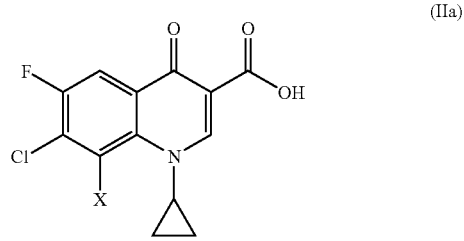

(b) contacting the compound having Formula VIa with an amount of HCl equal to about 0.1 to about 5 moles per mole of the compound having Formula VIIa at a temperature in the range from about room temperature to about 100° C., in a presence of methanol, to produce the fluoroquinolone carboxylic acid having Formula Ia; and (c) recovering the fluoroquinolone carboxylic acid having Formula Ia.

In yet another aspect, the crude product can comprise a mixture of enantiomers of the compound having Formula I or enantiomers of the compound having Formula IV, as tire case may be. One of the enantiomers is often more soluble in water than the other. Therefore, another aspect of the present invention comprises the separation of one of the enantiomers of a crude product by washing or dissolving the crude product with water, and recovering such an enantiomer from the aqueous phase.

Therefore, in another aspect of the present invention, a process of preparing an enantiomer of a fluoroquinolone having Formula I comprises: (a) contacting a first compound having Formula II with a second compound having Formula III to produce a crude enantiomeric mixture comprising enantiomers of the fluoroquinolone having Formula I; (b) recovering the crude enantiomeric mixture; (c) contacting the crude enantiomeric mixture thus recovered with water to produce an aqueous solution; and (d) recover the enantiomer of the fluoroquinolone having Formula I from the aqueous solution. In one embodiment, the step of contacting the crude enantiomeric mixture with water is carried out at a temperature in a range from about room temperature to about 80° C., or from about room temperature to about 50° C. In another embodiment, the step of contacting the crude enantiomeric mixture with water is carried out at about room temperature.

In still another aspect, a process of preparing an enantiomer of a fluoroquinolone having Formula IV comprises; (a) contacting a first compound having Formula II with a third compound having Formula V to produce a fourth compound having Formula VI; (b) contacting the fourth compound with a catalyst capable of assisting a cleavage of a protecting group from the $R^5$ group, to produce a crude enantiomeric mixture of fluoroquinolones having Formula IV; (c) recovering the crude enantiomeric mixture; (c) contacting the crude enantiomeric mixture thus recovered with water to produce an aqueous solution; and (d) recover the enantiomer of the fluoroquinolone having Formula IV from the aqueous solution; wherein X has the meaning disclosed above. In one embodiment, the step of contacting the crude enantiomeric mixture with water is carried out at a temperature in a range from about room temperature to about 80° C., or from about room temperature to about 50° C. In another embodiment, the step of contacting the crude enantiomeric mixture with water is carried out at about room temperature.

In a further aspect the present invention provides a process for preparing fluoroquinolones having Formula I. The process comprises: (a) contacting a compound having Formula XIII with a compound having Formula III to produce a compound having Formula XIV; and (b) halogenating the compound having Formula XIV with a halogenating agent to produce the fluoroquinolones having Formula I; wherein $R^1$ is selected from the group consisting of hydrogen, unsubstituted lower alkyl groups, substituted lower alkyl groups, cycloalkyl groups, unsubstituted $C_5$-$C_{24}$ and groups, substituted $C_5$-$C_{24}$ aryl groups, unsubstituted $C_5$-$C_{24}$ heteroaryl groups, substituted $C_5$-$C_{24}$ heteroaryl groups, and groups that can be hydrolyzed in living bodies; $R^2$ is selected from the group consisting of hydrogen, unsubstituted amino group, and amino groups substituted with one or two lower alkyl groups; $R^3$ is selected from the group consisting of hydrogen, unsubstituted lower alkyl groups, substituted lower alkyl groups, cycloalkyl groups, unsubstituted lower alkoxy groups, substituted lower alkoxy groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, unsubstituted $C_5$-$C_{24}$ aryloxy groups, substituted $C_5$-$C_{24}$ aryloxy groups, unsubstituted $C_5$-$C_{24}$ heteroaryloxy groups, substituted $C_5$-$C_{24}$ heteroaryloxy groups, and groups that can be hydrolyzed in living bodies; X is selected from the group consisting of halogen atoms; Y is selected from the group consisting of $CH_2$, O, S, SO, $SO_2$, and $NR^4$, wherein $R^4$ is selected from the group consisting of hydrogen, unsubstituted lower alkyl groups, substituted lower alkyl groups, and cycloalkyl groups; and Z is selected from the group consisting of oxygen and two hydrogen atoms. The compounds having Formulae XIII, III, and XIV are shown below.

(XIII)

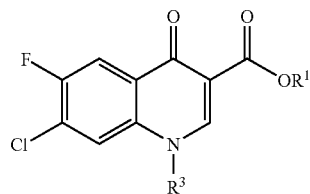

(III)

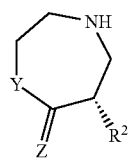

(XIV)

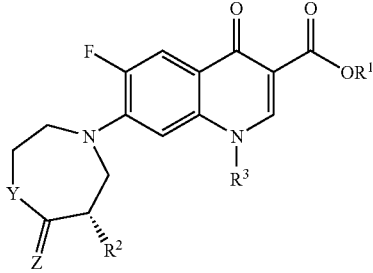

In one embodiment, a process for preparing a fluoroquinolone carboxylic acid having Formula Ia comprises: (a) contacting a compound having Formula XV with a compound having Formula VIIa at a temperature in the range from about room temperature to about 100° C. for a time from about 10 minutes to about 7 days, to produce a compound having Formula XVI; (b) chlorinating the compound having Formula XVI with a chlorinating agent to produce the fluoroquinolones having Formula XVII; (c) contacting the compound having Formula XVII with an amount of HCl equal to about 0.1 to about 5 moles per mole of the compound having Formula VIIa at a temperature in the range from about room temperature to about 100° C. in a presence of methanol, to produce the fluoroquinolone carboxylic acid having Formula Ia; and (d) recovering the fluoroquinolone carboxylic acid having Formula Ia. The compounds having Formulae XV, VIIa, XVI, and XVII are shown below.

(XV)

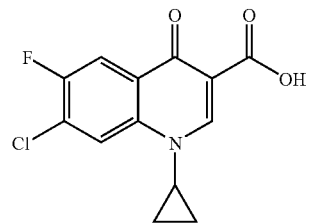

(VIIa)

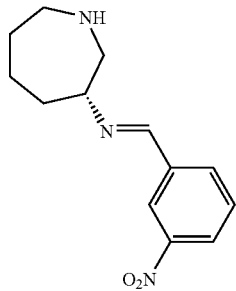

(XVI)

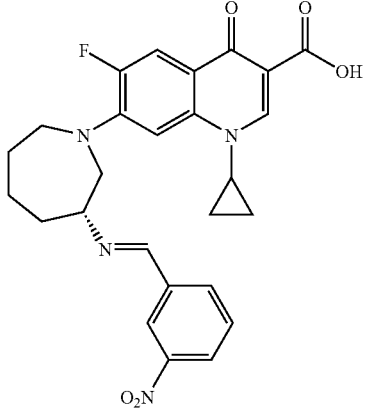

(XVII)

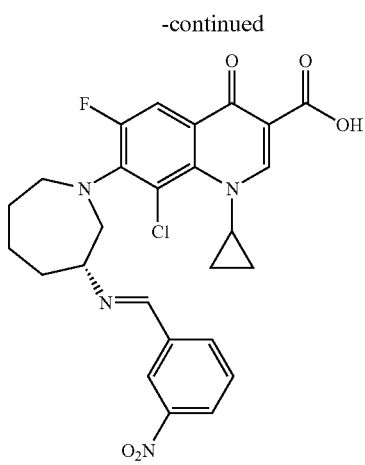

In one embodiment, the chlorinating agent is selected from the group consisting of sulfuryl chloride, chlorine, N-chlorosuccinic acid imide, and the like, in a suitable solvent, such as chloroform, dichloromethane, acetic acid, methanol, ethanol, and the like. The step of chlorinating can be carried out at a temperature in the range from about 0 to about 100° C. (when the step of chlorinating is carried out in a liquid medium, it may be preferred to employ a temperature lower than the boiling point of the solvent) for about 10 minutes to about 48 hours.

In yet another aspect, the present invention provides a fluoroquinolone having Formula I, Ia, or IV prepared by any appropriate process disclosed herein.

In some embodiments, a process of the present invention has advantages over the process disclosed in U.S. Pat. Nos. 5,385,900 and 5,447,926 in that such a process is simpler and does not require the last step of U.S. Pat. Nos. 5,385,900 and 5,447,926 for the attachment of a halogen atom to the position 8 on the compounds having Formulae I, Ia, and IV. This step requires the use of an excess amount of a halogenating agent such as sulfuryl chloride, chlorine, bromine, iodine, fluorine, N-chlorosuccinic acid imide, N-bromosuccinic acid imide, or the like. The use of such halogenating agents, especially in the gas phase, requires installation of precautionary measures in the manufacturing process, which would increase the complexity and cost of the manufacture.

Alternatively, in some other embodiment, a process of the present invention has advantages over the process disclosed in U.S. Pat. Nos. 5,385,900 and 5,447,926 because a process of the present invention effects a reaction on the material having Formula XIII, which is more readily available and more economically favorably than another material, identified as Compound 2 in these patents.

Compounds of this family of fluoroquinolones can be used effectively against the survival of microbial pathogens. For example, the compounds having Formula I, Ia, or IV are potent antimicrobial agents and are found to be effective against the survival of Gram-positive bacteria, such as *Bacillus subtilus, Staphylococcus aureus, Staphylococcus epidermis, Sarcina lutea, Streptococcus faecalis,* and *Micrococcus lysodeikticus;* Grain-negative bacteria, such as *Escherichia coli, Samonella typhi, Shigella flexneri, Pseudomonas aeruginosa, Kleisiela pneumonias, Proteus vulgaris, Proteus rettgeri,* and *Serratia marcesscens;* and a metricillin-resistant strain of *Streptococcus aureus.* See; e.g., U.S. Pat. Nos. 5,385,900 and 5,447,926; which are incorporated herein by reference in their entirety.

A fluoroquinolone compound prepared by any method disclosed herein can be formulated into an antimicrobial composition for topical, oral, systemic, ocular, or intraocular administration. Such a composition comprises a fluoroquinolone compound and an excipient appropriate for the administration, as can be determined by a person having skill in the art of pharmaceutical formulation for the applications disclosed above. For example, various excipients known in the art can be used to formulate a solution, suspension, dispersion, ointment, gel, capsule, or tablet. A fluoroquinolone compound prepared by any method disclosed herein is particularly suitable for a treatment, reduction, amelioration, or prevention of infections of the eye, ear, nose, throat, or respiratory system caused by bacteria, including, but not being limited to, those bacteria disclosed above. In one embodiment, such a fluoroquinolone is formulated into an ophthalmic solution, ointment, suspension, dispersion, or gel.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. A process of preparing a fluoroquinolone enantiomer having Formula IV or salts thereof, the method comprising:

(a) contacting a first compound having Formula II with a third compound having Formula V to produce a fourth compound having Formula VI, wherein the fluoroquinolone having Formula IV, the first compound, the third compound, and the fourth compound are represented by (IV)

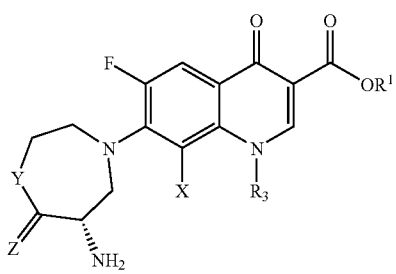

(II)

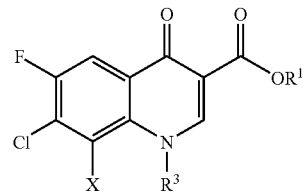

(V)

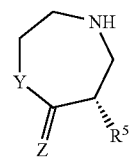

(VI)

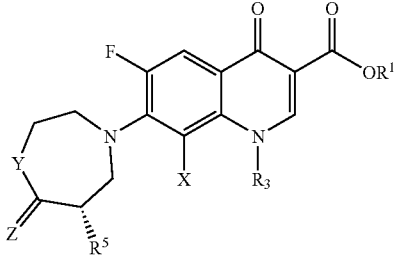

wherein $R^1$ is selected from the group consisting of hydrogen, unsubstituted lower alkyl groups, substituted lower alkyl groups, cycloalkyl groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, and groups that can be hydrolyzed in living bodies; $R^3$ is selected from the group consisting of hydrogen, unsubstituted lower alkyl groups, substituted lower alkyl groups, cycloalkyl groups, unsubstituted lower alkoxy groups, substituted lower alkoxy groups, unsubstituted $C_5$-$C_{24}$ aryl groups, substituted $C_5$-$C_{24}$ aryl groups, unsubstituted $C_5$-$C_{24}$ heteroaryl groups, substituted $C_5$-$C_{24}$ heteroaryl groups, unsubstituted $C_5$-$C_{24}$ aryloxy groups, substituted $C_5$-$C_{24}$ aryloxy groups, unsubstituted $C_5$-$C_{24}$ heteroaryloxy groups, substituted $C_5$-$C_{24}$ heteroaryloxy groups, and groups that can be hydrolyzed in living bodies; X is selected from the group consisting of halogen atoms; Y is $CH_2$; Z is selected from the group consisting of oxygen and two hydrogen atoms; and $R^5$ comprises a protected amino group having a formula or —$NR^6$, wherein $R^6$ comprises a protecting group that is capable of leaving the protected amino group —$NR^6$; and (b) contacting the fourth compound with a sufficient amount of a catalyst and at a condition sufficient to effect a cleavage of the protecting group $R^6$ from the —$NR^6$ group, to produce a fluoroquinolone having Formula IV; wherein the orientation of $R_2$ is preserved throughout the process.

2. The process of claim 1, wherein $R^1$ is selected from the group consisting of hydrogen, $C_1$-$C_5$ substituted and unsubstituted alkyl groups, $C_3$-$C_{10}$ cycloalkyl groups, $C_6$-$C_{14}$ substituted and unsubstituted aryl groups, $C_6$-$C_{14}$ substituted and unsubstituted heteroaryl groups, and groups that can be hydrolyzed in living bodies; $R^3$ is selected from the group consisting of hydrogen, $C_1$-$C_5$ substituted and unsubstituted alkyl groups, $C_3$-$C_{10}$ cycloalkyl groups, $C_1$-$C_5$ substituted and unsubstituted alkoxy groups, $C_5$-$C_{14}$ substituted and unsubstituted aryl groups, $C_5$-$C_{14}$ substituted and unsubstituted heteroaryl groups, and $C_5$-$C_{14}$ substituted and unsubstituted aryloxy groups; $R^6$ is selected from the group consisting of nitrophenylalkylidene, t-Boc, and Fmoc; and X is selected from the group consisting of Cl, F, and Br.

3. The process of claim 1, wherein $R^1$ is selected from the group consisting of hydrogen, $C_1$-$C_5$ substituted and unsubstituted alkyl groups and groups that can be hydrolyzed in living bodies; $R^3$ is selected from the group consisting of $C_3$-$C_{10}$ cycloalkyl groups; $R^6$ comprises a nitrophenylalkylidene group; X is selected from the group consisting of Cl and F; Y comprises $CH_2$; and Z comprises two hydrogen atoms.

4. The process of claim 1, wherein the catalyst is selected from the group consisting of acids and bases.

5. The process of claim 3, wherein the step of contacting is carried out at a temperature in a range from about room temperature to about 100° C.

6. The process of claim 3, wherein the catalyst is hydrochloric acid.

7. The process of claim 1, wherein the process further comprises recovering the enantiomer is carried out by recrystallization.

8. A process for preparing a fluoroquinolone carboxylic acid enantiomer having Formula Ia or salts thereof, the process comprising:

(a) contacting a compound having Formula IIa with a compound having Formula VIIa at a temperature in the range from about room temperature to about 100° C. for a time from about 10 minutes to about 7 days, to produce a compound having Formula VIa, wherein the fluoroquinolone having Formula Ia and the compounds having Formulae IIa, VIa, and VIIa are represent by

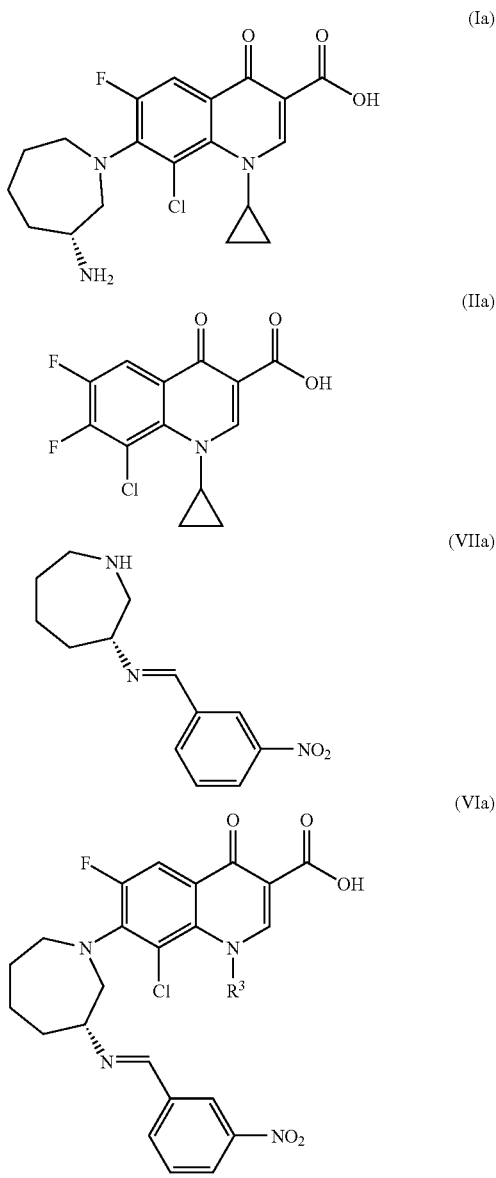

(b) contacting the compound having Formula VIa with an amount of HCl equal to about 0.1 to about 5 moles per mole of the compound having Formula VIIa at a temperature in the range from about room temperature to about 100° C., in a presence of methanol to produce the fluoroquinolone carboxylic acid having Formula Ia; and (c) recovering the fluoroquinolone carboxylic acid enantiomer having Formula Ia;

wherein the orientation of the amino group is presented throughout the process.

9. The process of claim 8, wherein the step of recovering the fluoroquinolone carboxylic acid enantiomer is carried out by recrystallization.

* * * * *

UNITED STATES PATENT AND TRADEMARK OFFICE
CERTIFICATE OF CORRECTION

PATENT NO. : 7,632,944 B2  Page 1 of 1
APPLICATION NO. : 11/626397
DATED : December 15, 2009
INVENTOR(S) : Arthur E. Harms It is certified that error appears in the above-identified patent and that said Letters Patent is hereby corrected as shown below:

In Col. 17, line 65
replace "C. for a time"
with "C for a time."

In Col. 18, line 56
replace "C., in a presence"
with "C, in a presence."

Signed and Sealed this

Sixth Day of April, 2010

David J. Kappos
*Director of the United States Patent and Trademark Office*